United States Patent [19]

Zinke

[11] 3,993,751

[45] Nov. 23, 1976

[54] PROCESS FOR STABILIZING THERAPEUTIC COMPOSITIONS AND ARTICLE

[75] Inventor: Charles D. Zinke, Fort Worth, Tex.

[73] Assignee: Cybersol, Inc., Dallas, Tex.

[22] Filed: Mar. 7, 1975

[21] Appl. No.: 556,281

Related U.S. Application Data

[62] Division of Ser. No. 308,021, Nov. 27, 1972, Pat. No. 3,878,664.

[52] U.S. Cl. .............................. 424/128; 424/153; 424/154; 424/156; 424/161
[51] Int. Cl.² ................. A61K 33/10; A61K 33/14; A61K 33/42
[58] Field of Search .......... 424/161, 153, 154, 156, 424/128

[56] References Cited
UNITED STATES PATENTS
1,616,202  2/1927  Shook ................................. 424/161

OTHER PUBLICATIONS

Verbruggen, Chem. Abst., vol. 72 (1970), p. 99376y.

*Primary Examiner*—Sam Rosen
*Attorney, Agent, or Firm*—Richards, Harris and Medlock

[57] ABSTRACT

A stabilized, therapeutic composition is provided which comprises an aqueous medium containing known amounts of $Na^+$, $K^+$, $HCO_3^-$, and $Cl^-$ wherein the pH of the solution is maintained between about 6 and 8.5 and the osmolality is maintained between about 170 and 460 by maintaining a gaseous mixture as a blanket over the solution during manufacture and storage, the gaseous mixture containing a sufficient amount of carbon dioxide to substantially equal the partial pressure of the carbon dioxide produced from equilibrium within the solution.

15 Claims, 1 Drawing Figure

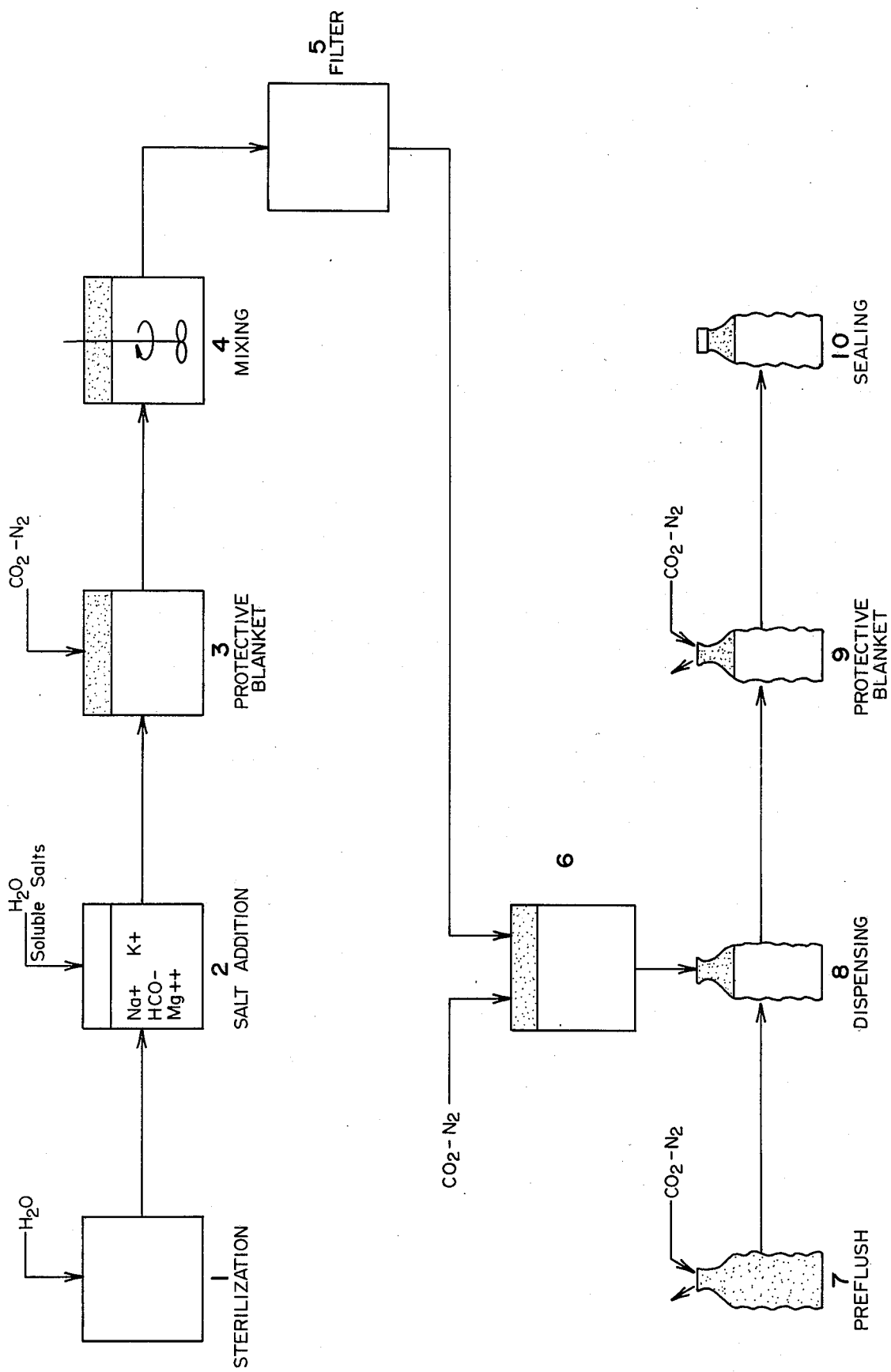

PROCESS FOR STABILIZING THERAPEUTIC COMPOSITIONS AND ARTICLE

This is a division of application Ser. No. 308,021, filed Nov. 27, 1972, now U.S. Pat. No. 3,878,664.

This invention relates to therapeutic compositions. In another aspect, this invention relates to a novel method of making a therapeutic composition. In still another aspect, this invention relates to a novel method of controlling the pH and osmolality of a therapeutic solution containing bicarbonate ions. In still another aspect, this invention relates to a novel means of containing a therapeutic solution of bicarbonate ion which will maintain the therapeutic solution at a constant pH and osmolality.

After accidental or elective operative injury to human patients, there occurs a decrease in the hemoglobin concentration, an elevation in the erythrocyte sedimentation rate of peripheral blood, and a loss of red blood cells from the effective blood volume. These events are recognized as anemia. Also, immediately subsequent to the injury, the white cell count is usually elevated, and the thrombocyte count is decreased, implicating pancytic mechanisms.

The administration of whole blood is useful to rectify the pancytic changes. However, most surgeons have been unable to maintain adequate quantities of peripheral total hemoglobin, red blood cells, and thrombocytes through the use of whole blood, even when quantities far in excess of that lost by bleeding are infused. Furthermore, it is known that the collection and storage of whole blood generally produces a hyperosmolar, acidic water solution as the result of changes in the red blood cells and blood water during collection and storage. Other disadvantages in the use of whole blood include its expense, and it may produce unwanted immunohematological responses in the recipient.

The surgeon and anesthesiologist have traditionally had four other choices instead of whole blood infusion to correct the above-described adversities. The four other choices include the administration of (1) plasma, (2) separated (packed) erythrocytes, (3) synthetic water solutions, or (4) synthetic water solutions containing synthetic protein. Plasma has some of the disadvantages of whole blood. Separated erythrocytes, besides being expensive, have the disadvantage of decrease in functional and structural life after re-infusion.

In recent years, synthetic water solutions with or without protein have been utilized to maintain the circulating blood volume and for maintenance of blood pressure. This is accomplished by replacing or attempting to replace that extracellular water which is lost to urine formation, in the wound, in respired air, and through the skin, and furthermore, by providing an amount sufficient to compensate for the enhancement in blood volume capacitance secondary to anesthetic agents. The first synthetic water solutions developed in the prior art emphasized ionic content, particularly sodium chloride, with little regard to other physiochemical requirements. However, the use of such materials do not achieve effective blood volume and extracellular water maintenance without excessive water administration and water retention. These excesses contribute to many vexations which extend the patient recovery time. Such vexations include gastro-intestinal water retention with hyptonia, ventilatory and other pulmonary problems, aberrations in urine volumes, muscular weaknesses, and sometimes cerebral disorientation.

Some of these conventionally utilized water solutions include sterile, U.S.P. water for injection, normal saline solutions, dextrose (5%) in saline or water, and solutions containing so-called bicarbonate precursors such as Lactated Ringer's. The latter types of solutions contain materials which are said to be bicarbonate precursors in that they are designed to release sodium ions after they have been infused into the bloodstream.

Recently, an improved synthetic water solution has been developed which overcomes many of the deficiencies of the prior art solutions, and its use reduces the above-described vexations which extend the patient recovery time. This improved therapeutic solution is disclosed in U.S. Pat. No. 3,676,553, and depends for its effectiveness upon the maintenance of proper osmolal pressure, proper pH, and proper ionic content. Since osmolal pressure and pH of a synthetic water solution injected into the bloodstream are dependent upon the total number of active soluble particles moving with varying speeds in the solution, the selection of solutes for the above-described novel synthetic water solutions was accomplished by utilizing the most rapidly moving hydrated solutes with optimal activity coefficients, but yet which are compatible with physiological waters of extracellular water and intracellular water. This new therapeutic composition utilizes sodium as its primary cation since sodium is recognized widely as the cation with primary activity in the extracellular water. The novel composition utilizes chloride as the principal anion, since chloride is the principal anion in extracellular water. The chloride enhances retention of intracellular potassium, the leading cation of the intracellular water. Futhermore, the abovedescribed therapeutic composition contains potassium in quantities preferably equal to its mean concentration in extracellular water including the water of the circulating red cell mass. Free bicarbonate ion is utilized in this new therapeutic composition because free bicarbonate is an essential solute in both extracellular water and intracellular water and causes potassium to shift into the cells. The novel therapeutic composition can contain other ions such as magnesium ($Mg^{++}$) and/or ($Ca^{++}$) as the principal minor solute cation and phosphate ($HPO_4^=$) and/or sulfate ($SO_4^=$) as the principal minor solution anion.

Thus, the bicarbonate ion which is present in the above-described novel therapeutic composition is not the conventional bicarbonate precursor such as sodium lactate, but is true bicarbonate ion. Evidence shows that in vitro ionization of sodium lactate which is utilized in synthetic water solutions such as Lactated Ringer's rarely exceeds about 70%. Furthermore, in order to accomplish the physiochemical purpose of causing potassium to shift into cells, the bicarbonate which is present in the synthetic water solutions must be in the form of bicarbonate ion and not in the form of the conventional precursors therefor. Thus, the physiochemical and physiological requisites for bicarbonate in the solution are satisfied by true bicarbonate solute alone. As set forth in the above-identified patent, when the novel therapeutic composition is utilized parenterally in conjunction with accidental or elective operative injury, the concentration of the above-described solutes are adjusted so that the solution has an osmolality of about 300 milliosmoles per liter (mOsm/L) and a pH of from about 7 to 7.6, preferably about 7.2. Furthermore, the osmolality and the pH of the above-described novel solution can be adjusted for other uses. For example, solutions having an osmolality of less than about 290 can be designed to move into the cells; thus, such solutions are usable in treatment of heat stroke or situations causing excessive sweating. Furthermore, solutions having an osmolality in excess of about 310 can be designed to attract water out of the cells. As a result, such solutions are useful, for example, in the treatment of overdoses of barbituates or any situation resulting in the unusual accumulation of water within the cells.

In general, the above-described improved therapeutic composition comprises an aqueous medium containing from about 75 to 150 millimoles of $Na^+$, about 5 to 50 millimoles of $K^+$, about 5–50 millimoles of $HCO_3^-$, about 75–150 millimoles of $Cl^-$, and preferably contains about 1–30 millimoles of $Mg^{++}$ and/or $Ca^{++}$ and about 1–30 millimoles of $HPO_4^=$ and/or $SO_4^=$. The solution can have a varied pH and an osmolality in the range of from about 170 to 460, depending on its use.

Great care must be taken when manufacturing this novel composition, especially in view of the fact that it is relatively difficult to maintain desired concentration of true bicarbonate ion in solution due to its sensitivity to environmental changes. More specifically, the bicarbonate ion in solution is in constant equilibrium with water and $CO_2$, and slight changes of temperature and pressure during manufacture and storage of the solution can result in an undesirable shift in the equilibrium and a loss of the true bicarbonate ion from the solution.

Accordingly, one object of this invention is to provide a novel process for making an aqueous therapeutic composition containing true bicarbonate ion.

Another object of this invention is to provide a novel process for stabilizing an aqueous therapeutic composition containing true bicarbonate solute.

A further object of this invention is to provide a novel container means for enclosing an aqueous therapeutic solution containing a regulated amount of bicarbonate ion.

According to one embodiment of this invention, a method of controlling the osmolality and the pH of an aqueous therapeutic composition containing a known quantity of bicarbonate ion is provided by maintaining a gaseous blanket over the said solution, said gaseous blanket containing carbon dioxide in a sufficient amount to prevent the loss of bicarbonate ion from solution. The gaseous blanket preferably contains carbon dioxide and at least one other inert gas, the carbon dioxide being present in a sufficient amount to substantially equal the partial pressure of the carbon dioxide produced from equilibrium within said solution at the temperature of said solution.

More specifically, one embodiment of this invention comprises a method of maintaining the pH of a therapeutic composition within the range of from about 6 to about 8.5, which composition comprises an aqueous medium containing about 75–150 millimoles of $Na^+$, about 5–50 millimoles of $K^+$, about 5–50 millimoles of $HCO_3^-$, about 75–150 millimoles of $Cl^-$, up to about 30 millimoles of $Mg^{++}$, and/or $Ca^{++}$ and up to about 30 millimoles of $HPO_4^=$, and/or $SO_4^=$, and having an osmolality in the range of about 170–460, by maintaining a gaseous blanket over the solution which comprises a mixture of carbon dioxide and another inert gas or gases, the carbon dioxide being present in the gaseous mixture in an amount to maintain a pH in the solution in the range of from about 6 to about 8.5 at a temperature in the range of from about 25° C to about 50° C.

According to another embodiment of this invention, a novel method is provided for manufacturing an aqueous therapeutic composition minor cation solute and a predetermined amount of bicarbonate ion solute which includes initially providing a sterile water volume and thereafter dissolving water soluble salts containing ions which include bicarbonate in the solution, and next, blanketing the resulting solution with a mixture of carbon dioxide and inert gas, such as nitrogen, wherein the carbon dioxide is present in the gaseous mixture in an amount to provide a partial pressure on the liquid which is substantially equal to the partial pressure which is produced from equilibrium in the solution at the solution temperature and thereafter, agitating the solution to assure complete dissolution of all the water-soluble salts therein. The stabilized solution is then dispensed within pyrogen-free containers which have been preflushed with the above-described gaseous mixture, and then covered with the above-described gaseous mixture, and sealed. The stabilized solution while blanketed by the above-described gaseous mixture can be sterilized by conventional techniques. In accordance with a preferred embodiment of this invention, the solution is filtered by passing it through membrane filters containing pores generally less than 1 micron in diameter before it is dispensed within the pyrogenfree containers.

Accordng to another embodiment of this invention, a novel shipping and dispensing container means is provided for an aqueous therapeutic composition containing bicarbonate ions which comprises a container having the solution as a liquid phase and the above-described gaseous mixture as a protective blanket gaseous phase sealed therewithin.

The therapeutic composition made in the scope of this invention can be administered orally but preferably parenterally. The therapeutic composition made in accordance with this invention is preferably equi-osmolar with respect to the mean osmolality of extracellular water (ECW) and is designed to minimize water movements into fixed cells after operative, anesthetic and accidental trauma. In addition, the preferred parenteral solution diminishes loss of functional decrements in all body systems, particularly heart and circulating fluids, lung, kidney, gastrointestinal tract and brain.

The therapeutic composition made in accordance with this invention contains sodium ($Na^+$) and potassium ($K^+$) as the principal major cation solutes, and true bicarbonate ($HCO_3^-$) and chloride ($Cl^-$) as the primary anion solutes. In addition, other solutes such as magnesium ($Mg^{++}$) and/or calcium ($Ca^{++}$), phosphate ($HPO_4^=$) and/or sulfate ($SO_4^=$) amd IOA (impermeable organic anions) can be present in the therapeutic composition all in accordance with the teachings of U.S. Pat. No. 3,676,553, which is hereby incorporated by reference into this specification. In addition, the therapeutic solution made in accordance with this invention can have an osmolality within the range of from about 170 to about 460, preferably from about 260 to about 340, more preferably from 290 to 310, and most preferably about 300. It is noted that osmolality as used in the scope of this invention means the specific number of millimoles dissolved in one liter of water. The osmolality can be directly measured with a conventional osmometer such as manufactured by Advanced Instruments Inc. of Newton Highlands, Massachusetts. Generally, the solutions made in accordance with this invention have a measured osmolality in the range of from about 170 to about 460 at 37° C. The osmometer is basically a freezing point depression apparatus which utilizes a standard reference solution. Standard aqueous solutions of NaCl can be made up in a conventional manner. For example, a standard theoretical 300 milliosmole NaCl solution consists of 150 millimoles per liter of NaCl. Another standard which can be used to measure the osmolality is normal human blood plasma which has an osmolality of 298 milliosmoles per liter at 37° C.

In addition, the pH of the therapeutic solution made in accordance with this invention can range from about 6.0 to about 8.5 and is preferably within the range of from 7.0 to 8.0, and more preferably in the range of from 7.0 to 7.6.

The therapeutic composition manufactured and packaged in accordance with this invention can contain varying amounts of the principal and minor anion solutes, and thus a wide range of osmolality and pH, but yet be stable at such concentrations. Generally, the concentration of the ions in the therapeutic composition made in accordance with the subject invention can be as set forth in Table I below:

Known water soluble salts containing the ions which are desired for the therapeutic composition can be utilized. Examples of such salts include NaCl, KCl, $NaHCO_3$, $KHCO_3$, $MgCl_2$, $CaCl_2$, $Na_2SO_4$, $Na_2HPO_4$, $MgSO_4$ and $K_2HPO_4$. In addition, if desired, a chelating agent such as disodium edetate [disodium (ethylene dinitrilo) tetraacetate] can be added at this point. The chelating agent will serve to sequester any trace amounts of metal ions such as tin, zinc and aluminum ions and prevent the hydroxide formation and precipitation thereof. Typical solutions produced in accordance with this invention are made by the addition of sodium chloride, potassium chloride, magnesium sulfate, disodium edetate, and sodium bicarbonate to the sterile water. It is noted that it is preferable to add the sodium bicarbonate to the water after the other salts have been dissolved therein. In essence, it is preferably to add the sodium bicarbonate to the solution which contains the other dissolved salts so that the water has multiple ions in solution. This addition sequence has the effect of preventing any unwanted reaction between the magnesium salts, such as magnesium chloride and bicarbonate ions which may form a resulting precipitate of the magnesium carbonate, for example.

After the salt addition to the water, the solution is

TABLE I

| Ion | Concentration (Millimoles/Liter) | | | |
|---|---|---|---|---|
| | Minimum | Maximum | Preferred | Most Preferred |
| Sodium ($Na^+$) | 75 | 150 | 85–140 | 128 |
| Potassium ($K^+$) | 5 | 50 | 10–40 | 17 |
| Bicarbonate ($HCO_3^-$) | 5 | 50 | 10–40 | 25 |
| Chloride ($Cl^-$) | 75 | 150 | 85–130 | 120 |
| Magnesium ($Mg^{++}$), Calcium ($Ca^{++}$) | 0 | 30 | 2–20 | 5 |
| Phosphate ($HPO_4^=$), Sulfate ($SO_4^=$) | 0 | 30 | 2–20 | 5 |

This invention can be more easily understod from a study of the drawing which comprises a schematic diagram depicting a preferred procedure for manufacturing the therapeutic composition in the scope of this invention.

Now referring to the drawing, a typical batch type reaction process for producing a therapetuc composition of the scope of this invention is schematically illustrated. It is noted that the process of the subject invention can be practiced as a continuous process if desired; however, it will be described in detail in terms of a batch process.

Now referring to the drawing in detail, initially a predetermined volume of U.S.P. water is obtained. Preferably, distilled water is added to a pressure-sealable batch reactor and sterilized to removed pyrogen contaminants therefrom. A suitable sterilization cycle includes heating the distilled water to a temperature of 121° C for a period of at least an hour. Any other heating cycle can be utilized which is suitable for removing pyrogen contaminants from the water. A suitable batch reactor comprises a pressure sealable reactor equipped with an internal stirring mechanism and suitable means to heat the interior thereof such as a steam jacket.

After the sterilization step, the resulting pyrogen free water is cooled to a temperature within the range of from about 25° to about 50° C and more preferably within the range of from about 25° to about 40° C.

After the water has been cooled, predetermined amounts of salts can be added to the interior of the reactor to produce a solution of a desired osmolality.

then blanketed (step 3 in the drawing) with a carbon dioxide-inert gas atmosphere, preferably at one atmosphere pressure. And then thoroughly agitated (step 4 in the drawing) to assure complete dissolution of all of the salts in the sterile water.

The gaseous protective blanket contains sufficient carbon dioxide to prevent loss of carbon dioxide from the solution which is normally produced from equilibrium conditions of the bicarbonate in solution. In essence, the carbon dioxide is present in the gaseous mixture in an amount to provide a partial pressure on the liquid which is substantially equal to the partial pressure which is produced from equilibrium of bicarbonate in the solution at the mixing temperature.

More specifically, the carbon dioxide is present in the gaseous blanket in an amount to maintain a pH of the solution in the range of from about 6 to about 8.5 at a temperature in the range of from about 25° to about 50°C (the temperature of the solution). As set forth above, the therapeutic solution of the subject invention can contain bicarbonate ion in the range of from about 5 to about 50 millimoles per liter. Accordingly, from about 0.0007 to about 0.92 atmospheres of carbon dioxide are necessary to maintain a pH of the solution within a pH in the range of from about 6 to about 8.5. The amount of carbon dioxide in the gaseous blanket can be derived by simple physical chemical calculations.

The remaining gaseous component in the gaseous protective blanket can comprise any inert gas which is nondeleterious to the solution. By "nondeleterious to the solution" it is meant that the gas should not react with the solution and it should not change the osmolality nor the pH of the solution when contacted therewith in any amounts.

Suitable gases include nitrogen, argon, helium, and the like. Because of its pharmaceutical acceptability and availability nitrogen is generally preferred as the component to be utilized in admixture with carbon dioxide in the protective gaseous blanket.

Furthermore, when used in the scope of this invention to define the relative amount of carbon dioxide is present in the gaseous blanket the term "partial pressure which is substantially equal to the partial pressure which is produced from equilibrium in the therapeutic solution" is understood to mean the partial pressure of carbon dioxide which is ultimately desired after the solution has been formed and the gaseous carbon dioxide blanket applied thereto.

In essence, the partial pressure of the carbon dioxide in the blanket can be adjusted to either stabilize the initial pH of the solution, or to actually contribute to the final pH of the solution. For example, in the latter situation, a solution can be initially formed to have a higher pH than that which is ultimately desired and the carbon dioxide in the gaseous blanket can be present in such amounts to actually function in part to yield a lower pH than that initially formed. In either case, the carbon dioxide in the gaseous blanket serves to stabilize the normal equilibrium breakdown of the bicarbonate in solution at the final desired pH.

As an example of various amounts of carbon dioxide which can be utilized in the protective blanket in the scope of this invention with a preferred solution containing an osmolality of about 300 such as set forth below in Table II, the data in Table III are provided.

TABLE II

| SOLUTE ION | Therapeutic Solution Having An Osmolality of 300 CONCENTRATION (Millimoles per liter) |
|---|---|
| $Na^+$ | 131 |
| $K^+$ | 14 |
| $Mg^{++}$ | 5 |
| $HCO_3^-$ | 18 |
| $Cl^-$ | 127 |
| $SO_4^=$ | 5 |

TABLE III

| pH | Moles of $CO_2$ | $CO_2$ Partial Pressure in Blanket (Atmospheres) |
|---|---|---|
| 6.0 | 0.011 | 0.329 |
| 6.1 | 0.00994 | 0.299 |
| 6.2 | 0.00891 | 0.274 |
| 6.3 | 0.00789 | 0.237 |
| 6.4 | 0.00687 | 0.207 |
| 6.5 | 0.00594 | 0.179 |
| 6.6 | 0.00505 | 0.152 |
| 6.7 | 0.00427 | 0.128 |
| 6.8 | 0.00356 | 0.107 |
| 6.9 | 0.00295 | 0.0887 |
| 7.0 | 0.00242 | 0.0728 |
| 7.1 | 0.00198 | 0.0596 |
| 7.2 | 0.00161 | 0.0484 |
| 7.3 | 0.00130 | 0.0393 |
| 7.4 | 0.00105 | 0.0315 |
| 7.5 | 0.000845 | 0.0254 |
| 7.6 | 0.000677 | 0.0204 |
| 7.7 | 0.000541 | 0.0163 |
| 7.8 | 0.000433 | 0.0130 |
| 7.9 | 0.000345 | 0.0104 |
| 8.0 | 0.000275 | 0.00829 |
| 8.1 | 0.000219 | 0.00661 |
| 8.2 | 0.000174 | 0.00526 |
| 8.3 | 0.000140 | 0.00420 |
| 8.4 | 0.000111 | 0.00334 |
| 8.5 | 0.000088 | 0.00266 |

As stated, the relative amount of carbon dioxide in the protective gas blanket can be determined by simple physical chemical calculations. However, as a general guide, Table IV is presented to illustrate preferred various amounts of carbon dioxide in the gaseous blanket which can be utilized with from 5 to 50 millimoles of bicarbonate at pH's from 6 to 8.5 and at a temperature in the range of from about 25° to about 50° C for the compositions made in the scope of this invention.

TABLE IV $CO_2$ NEEDED TO STABILIZE SOLUTION

PART 1

| Moles Bicarbonate Added to Solution | pH 6.0 | | pH 6.5 | | pH 7.0 | | pH 7.2 | |
|---|---|---|---|---|---|---|---|---|
| | Moles | Pressure (Atm) | Moles | Pressure (Atm) | Moles | Pressure (Atm) | Moles | Pressure (Atm) |
| 0.005 | 0.00304 | 0.0918 | 0.00165 | 0.0498 | 0.000674 | 0.0203 | 0.000446 | 0.0134 |
| 0.010 | 0.00688 | 0.183 | 0.00330 | 0.0993 | 0.001344 | 0.0405 | 0.000893 | 0.0268 |
| 0.015 | 0.00914 | 0.275 | 0.00494 | 0.149 | 0.00202 | 0.0609 | 0.00134 | 0.0404 |
| 0.020 | 0.0122 | 0.367 | 0.0066 | 0.199 | 0.00269 | 0.0810 | 0.00179 | 0.0438 |
| 0.025 | 0.01520 | 0.470 | 0.00825 | 0.249 | 0.00337 | 0.1013 | 0.00223 | 0.0672 |
| 0.030 | 0.01824 | 0.550 | 0.0099 | 0.298 | 0.00404 | 0.122 | 0.00267 | 0.0804 |
| 0.035 | 0.02130 | 0.639 | 0.0115 | 0.348 | 0.00471 | 0.142 | 0.00313 | 0.0942 |
| 0.040 | 0.02425 | 0.729 | 0.0132 | 0.397 | 0.00538 | 0.162 | 0.00357 | 0.1075 |
| 0.045 | 0.02740 | 0.825 | 0.0148 | 0.448 | 0.00607 | 0.183 | 0.00402 | 0.121 |
| 0.050 | 0.0304 | 0.918 | 0.0165 | 0.498 | 0.00673 | 0.203 | 0.00464 | 0.140 |

PART 2

| Moles Bicarbonate Added to Solution | pH 7.6 | | pH 8.0 | | pH 8.5 | |
|---|---|---|---|---|---|---|
| | Moles | Pressure (Atm) | Moles | Pressure (Atm) | Moles | Pressure (Atm) |
| 0.005 | 0.000188 | 0.00566 | 0.000076 | 0.00229 | 0.0000245 | 0.00074 |
| 0.010 | 0.000376 | 0.0103 | 0.000153 | 0.00462 | 0.000049 | 0.00148 |
| 0.015 | 0.000564 | 0.0170 | 0.00023 | 0.00683 | 0.000074 | 0.00220 |
| 0.020 | 0.000754 | 0.0227 | 0.000307 | 0.00924 | 0.000098 | 0.00296 |
| 0.025 | 0.000939 | 0.0283 | 0.000382 | 0.0115 | 0.000112 | 0.00336 |
| 0.030 | 0.00103 | 0.0339 | 0.000458 | 0.0138 | 0.000147 | 0.00442 |
| 0.035 | 0.00132 | 0.0398 | 0.000536 | 0.0161 | 0.000172 | 0.00518 |
| 0.040 | 0.00150 | 0.0453 | 0.000611 | 0.0184 | 0.000196 | 0.00591 |

TABLE IV-continued

| 0.045 | 0.00169 | 0.0510 | 0.00069 | 0.0208 | 0.00022 | 0.0066 |
| 0.050 | 0.00196 | 0.0589 | 0.000794 | 0.0239 | 0.000253 | 0.0077 |

Thus, as can be seen, therapeutic solutions of various osmolalities and pH's can be admixed in accordance with this invention under protective blankets containing corresponding amounts of $CO_2$ which are substantially equal to the partial pressure which would be produced from equilibrium of the bicarbonate in each of the solutions at a temperature of from 25° to 50° C.

Now again referring to the drawing, the solution is agitated sufficiently to assure the dissolution of the salts for a period sufficient to assure the formation of the solution in the scope of this invention. It is noted that the agitation inherently exposes much of the surface of the liquid to the atmosphere within the vessel and would normally hasten the unwanted breakdown of the bicarbonate in the solution. However, the protective blanket of $CO_2$ - inert gas utilized as the atmosphere within the agitated vessel will stabilize the equilibrium breakdown of bicarbonate in the solution.

It is noted that in some instances wherein a chelating agent such as disodium edetate is not added to the solution, and it is desired to rid the solution of any trace amounts of undesirable metal ions such as tin, zinc and aluminum, the solution should be heated or maintained at a temperature of about 40° C after it is mixed in step 4 to cause the unwanted metal hydroxides to precipitate therefrom. The precipitate will be removed by the filter step set forth schematically as step 5 in the drawing.

After the agitation step, it is preferable to check the pH of the agitated solution. Minor pH adjustments can be made at this time with known acids or bases, e.g., HCl, NaOH, etc., whose reactions with the solution will not produce ion solutes different from the above-described solutes which can be present in the solution.

After the solution has been formed by the admixing step, it is filtered to remove any bacteria, fungi, and other particulate contaminants therefrom. The solution is passed through a filter containing pores which are generally less than 1 micron in diameter. It is noted that bacteria have a size of between 1 and 2 microns and the filtration step should remove any bacteria, if present, from the solution. The solution can be passed through 1 or more filter membranes in series if desired. Generally, a suitable filtering system includes a pair of membrane filters in series. Suitable membrane filters include the ceramic membrane filters manufactured by The Millipore Corporation, Bedford, Massachusetts. These membranes have a 0.22 micron porosity.

The filtered solution is then passed into a suitable holding tank (shown as step 6 in the drawing). Again, it is generally preferable to maintain the carbon dioxide-inert gas blanket over the filtered solution within the holding tank. It is noted that the solution which has been filtered and bacteria, fungi, and other particulate matter removed therefrom still can be unstable when placed in contact with the atmosphere. For example, if one were to place a beaker of the 300 osmolality solution which is set forth in Table II above in contact with the atmosphere at room temperature, it would change approximately 0.5 pH point per hour. In addition, as the pH changes and carbon dioxide is lost from the solution into the atmosphere, the resulting osmolality of the solution will change correspondingly in a deleterious manner. The protective $CO_2$-inert gas blanket which is used in the scope of this invention during the processing and storage steps will prevent such deleterious change in pH and osmolality of the therapeutic composition.

The stable sterile therapeutic composition which has been formed and retained in holding tank (illustrated as step 6 in the drawing) can be dispensed in any suitable container known in the art. The containers can be of a suitable volume, for example, conventional 500 or 1000 milliliter infusion bottles. The containers can comprise glass containers or therapeutically acceptable plastic containers of various sizes and shapes including flexible bag-type containers made of polyvinyl materials, such as polyvinyl acetate having integral outlet tubing attached thereto.

Thus, any pharmacologically acceptable container known in the art can be utilized to bottle the therapeutic solution made in the scope of this invention. All such containers are air tight and capable of receiving a liquid and gaseous material under one atmosphere pressure. In addition, the container materials should obviously not react with the therapeutic composition. When bottling the therapeutic compositions made within the scope of this invention which has a pH of 7 or higher, and when utilizing glass bottles for containers, it is preferred to use a glass material which will not react with the alkaline solution. Suitable glass materials include the borosilicate type glass bottles.

When filling the container with the stabilized therapeutic solution manufactured in accordance with this invention, it is preferred to initially preflush the sterile container with the same carbon dioxide-nitrogen mixture which is utilized in manufacturing the solution such as set forth schematically in step 7 of the drawing. The preflushed bottle is then passed to a filling stage wherein the stabilized therapeutic composition is dispensed therewithin, such as set forth schematically in step 8 of the drawing. After the stabilized therapeutic solution has been dispensed into the bottle, the bottle is then passed to another stage wherein the $CO_2-N_2$ gas blanket is again passed over the liquid level within the container as shown schematically in step 9 of the drawing. After the $CO_2-N_2$ gas blanket is formed over the liquid level in the container, the container is instantaneously sealed as set forth schematically in step 10 of the drawing. When utilizing a typical 500 milliliter glass infusion bottle, the bottle is capped with a solid black rubber stopper having an epoxy coating on the lower portion thereof adjacent the gas blanket. Any conventional lid is placed over the glass and stopper, such as aluminum tamper-proof seal which is well known in the art. Basically, an aluminum disc is placed over the top of the stopper and then an aluminum cap is placed over the aluminum disc. Any other suitable conventionally available stopper means can be utilized.

As set forth above, any other suitable container means can be utilized, such as a flexible bag having integrally connected dispensing tubing for administering parenteral solutions. It is only necessary in the scope of this invention that the gaseous atmosphere inside the container comprise the $CO_2$-inert gas mixture which is utilized in manufacturing the solution as set forth above. The resulting article comprises a sealed container having a liquid phase comprising the therapeutic composition containing a known amount of bicarbonate ion and a gaseous phase comprising carbon dioxide inert gas and containing suffficient carbon dioxide to maintain the pH of the solution in the range of from about 6 to about 8.5 as desired, and a temperature range of from about 25 to 50° C. The resulting bottle can be subjected to temperature extremes (above and below the above-stated range) to which pharmacological infusion materials may be normally subjected during shipment and storage. These temperature extremes will not affect the resulting composition. It is only desirable that before the solution is utilized that it be equilibrated at a temperature in the range of from 25° to 50° C and preferably about 25°–40° C. The resulting liquid therapeutic composition can be parenterally administered to the patient and the physician will be assured that the solution contains true bicarbonate ions and will enter the patient at a known pH and osmolality.

The above-described preferred embodiment for producing the therapeutic composition of the subject invention which includes the filtration step comprises a process which achieves the highest level of pharmaceutical elegance. However, it is to be noted that other sterilization techniques can be used in the scope of this invention. In essence, any U.S.P. accepted sterilization standard can be utilized to sterilize the stabilized composition produced in the scope of this invention (the therapeutic composition stabilized by the described gaseous blanket). Such procedures which conform to U.S.P. standards are well known and include sterilization of containers with ethylene oxide gas prior to filling irradiation and autoclaving. Such procedures can be utilized alone or in conjunction with the filtration step. For example, when autoclaving is used either alone or in conjunction with the above-described preferred filtration step, the stabilized therapeutic composition having the above-described gaseous blanket positioned thereover can be autoclaved, for example, in the infusion bottles after it has been dispensed therewithin. A suitable autoclave cycle will include heating the material to 121° C for 24 minutes, for example. Thus, it is not absolutely necessary to utilize the filtration step to sterilize the stabilized therapeutic composition in accordance with the broad aspect of this invention. However, the filtration step is included in the preferred process carried out in the scope of this invention.

The following examples are given to better facilitate the understanding of this invention and are not intended to limit the scope thereof.

EXAMPLE 1

7,500 Five hundred milliliter infusion bottles (with a 2% overfill) of an injectible therapeutic composition having an osmolality of 300 and a pH of 7.2 were manufactured in accordance with this invention by initially charging 3, 531, 117 grams of U.S.P. water (water for injection) into a 1,000 gallon compounding tank. The 1,000 gallon compounding tank was equipped with an internal stirrer, a sealable cover with a bleeder valve, a bottom drain, and a heating jacket operated by steam. After the water was added to the compounding tank, the stirrer was activated. Next, the compounding tank was heated by the steam jacket to a temperature of 85° C with the hatch open. After the water had reached 85° C, the hatch cover was closed and sealed but the bleeder valve remained open. The water was heated further until it reached a temperature of between 95° and 98° C and thereafter the bleeder valve was closed. After the bleeder valve was closed, the water was heated to 121° C for 1 hour.

Next, the contents of the tank were cooled to a temperature of between 25° and 30° C and vented. After the solution had cooled the following materials were added to the sterilized water: 23,576 grams of sodium chloride; 3,727 grams of potassium chloride; 4,398 grams of magnesium sulfate heptahydrate; and 1,785 grams of disodium edetate. Next, the stirring mechanism was turned off and with the solution quiescent, 5,397 grams of sodium bicarbonate was added thereto. After the sodium bicarbonate was added to the solution, the solution was covered with a gaseous blanket which consisted of about 0.05 atmospheres of $CO_2$ and 0.95 atmospheres of nitrogen and the compounding tank was sealed. Thus, the ratio of carbon dioxide to nitrogen was in the range of from 1:10 to 1:20. The batch was agitated with the stirrer for about 30 minutes, and then a sample taken from the lower drain of the compounding tank and the pH checked. After this, the solution was drained from the compounding tank and passed through two membrane filters, each having a 0.22 micron porosity. The membrane filters were in series. At the beginning of the filtration, the nitrogen pressure was increased to 30 psig on the solution to test the integrity of the filters and thereafter the filtration proceeded under one atmosphere pressure. The filtrate was collected in a reservoir and blanketed with the abovedescribed carbon dioxide-nitrogen blanket. The reservoir was connected to a bottling apparatus which dispensed 500 milliliters (plus a 2% overfill) to each of the infusion bottles. Prior to the time that the bottles had received the therapeutic composition, they had been preflushed by passing a steady stream of the abovedescribed $CO_2$—$N_2$ mixture therein. After each of the bottles had received the 500 milliliters of therapeutic composition, the solution within each of the bottles was again blanketed with the above-described $CO_2$—$N_2$ mixture and then immediately sealed. Each bottle is inspected for particulate matter by passing it through an illuminated path in front of a black and white background. In addition, sample bottles from the filling operation were removed from the filling operation at regular intervals and subjected to standard quality control and toxicity testing. The material was found to be sterile.

EXAMPLE 2

The basic procedure set forth in Example 1 above can be utilized to produce any of the therapeutic compositions in the scope of this invention by altering the amounts of solute in the water and the concentration of carbon dioxide in the protective blanket utilized in the manufacture and bottling of the solutions. For example, a typical 500 ml unit of a solution in the scope of this invention having an osmolality of 290, has the basic formulation as set forth in Table V below.

TABLE V

| COMPONENT | TYPICAL UNIT IN GRAMS PER 500 Ml |
|---|---|
| Sodium Chloride | 3.244 |
| Sodium Bicarbonate | 0.672 |

TABLE V-continued

| COMPONENT | TYPICAL UNIT IN GRAMS PER 500 Ml |
|---|---|
| Potassium Chloride | 0.503 |
| Magnesium Sulfate Heptahydrate | 0.554 |

A typical 500 ml unit of a solution having an osmolality of 310 has the formulation set forth in Table VI below:

TABLE VI

| COMPONENT | TYPICAL UNIT IN GRAMS PER 500 Ml |
|---|---|
| Sodium Chloride | 3.360 |
| Sodium Bicarbonate | 0.840 |
| Potassium Chloride | 0.541 |
| Magnesium Sulfate Heptahydrate | 0.678 |

Furthermore, a typical 500 ml unit of a solution having an osmolality of 200 has the formulation set forth in Table VII below:

TABLE VII

| COMPONENT | TYPICAL UNIT IN GRAMS PER 500 Ml |
|---|---|
| Sodium Chloride | 0.245 |
| Sodium Bicarbonate | 0.514 |
| Potassium Chloride | 0.355 |
| Magnesium Sulfate Heptahydrate | 0.418 |

The solutions set forth in Tables V – VII can be maintained at any suitable pH from 6 – 8.5 by maintaining the proper ratio of $CO_2$ to inert gas in the protective blanket used over the solution during the blanketing steps as set forth in the procedure in Example 1.

It is noted that in all of the formulations set forth in Tables V – VII, 0.05% W/V disodium edetate can be added if desired.

While this invention has been described in relation to its preferred embodiments, it is to be understood that various modifications thereof will now be apparent to one skilled in the art upon reading this specification and it is intended to cover such modifications as fall within the scope of the appended claims.

I claim:

1. An article comprising a container having a liquid phase and gaseous phase hermetically sealed therewithin, said liquid phase comprising an injectable aqueous solution comprising about 75 to about 150 millimoles of sodium cation, about 5 to about 50 millimoles of potassium cation, about 5 to about 50 millimoles of bicarbonate ion, and about 75 to about 150 millimoles of chloride ion and having an osmolality in the range of from about 170 to about 460, and a pH in the range of from about 6 to about 8.5, said gaseous phase being in contact with said liquid phase and comprising a mixture of carbon dioxide and inert gas, said carbon dioxide being present in an amount to impart substantially equal pressure to the partial pressure of carbon dioxide from said liquid due to equilibrium within said liquid at a temperature in the range of about 25° to about 50° C.

2. The article of claim 1 wherein said gaseous phase is at one atmosphere pressure and said carbon dioxide in said gaseous phase is present in an amount to provide partial pressure in the range of from about 0.0007 to about 0.92 atmospheres.

3. The article of claim 2 wherein said inert gas is nitrogen.

4. The article of claim 1 wherein said liquid phase is maintained at a pH in the range of from about 7 to about 7.6.

5. The article of claim 1 wherein said osmolality of said liquid phase is about 300.

6. The article of claim 1 further comprising from about 1 to about 30 millimoles of a cation selected from the group consisting of magnesium, and calcium and from about 1 to about 30 millimoles of an ion selected from the group consisting of phosphate and sulfate incorporated into said liquid phase.

7. The article of claim 1 further comprising from about 1 to about 30 millimoles of a cation selected from the group consisting of magnesium and calcium in said liquid phase.

8. The article of claim 1 further comprising from about 1 to about 30 millimoles of phosphate anion or sulfate anion or a combination thereof incorporated into said liquid phase.

9. An article comprising a container having a liquid phase and a gaseous phase hermetically sealed therewithin, said liquid phase comprising an injectible aqueous solution containing a known quantity of bicarbonate ions, said gaseous phase being in contact with said liquid phase and being a material selected from carbon dioxide and inert gas, said carbon dioxide being present in an amount to prevent loss of bicarbonate ions from solution due to the equilibrium within said liquid at a temperature in the range of from about 25° to about 50° C.

10. The article of claim 9 wherein said injectible aqueous solution comprises about 75 to 150 millimoles per liter of sodium cation, about 5 to about 50 millimoles per liter of potassium cation, about 5 to about 50 millimoles per liter of bicarbonate ion, and about 75 to about 150 millimoles per liter of chloride ion, and has an osmolality in the range of from about 170 to about 460 and a pH in the range of from about 6 to about 8.5.

11. The article of claim 10 wherein said inert gas is nitrogen, said gaseous phase is at 1 atmosphere pressure, and said carbon dioxide in said gaseous phase is present in an amount to provide partial pressure in the rage of from about 0.0007 to about 0.92 atmospheres.

12. A method of stabilizing the osmolality and pH of an aqueous therapeutic solution at desired levels, which solution contains a known quantity of bicarbonate ion, said method comprising maintaining a gaseous mixture of carbon dioxide and an inert gas as a blanket over said solution, said gaseous mixture containing a sufficient amount of carbon dioxide to substantially equal the partial pressure of carbon dioxide produced from equilibrium within said solution at a temperature within the range of from about 25° to about 50° C.

13. The method of claim 12 wherein said aqueous solution comprises from about 75 to about 150 millimoles per liter of sodium cation, from about 5 to about 50 millimoles per liter of potassium cation, about 5 to about 50 millimoles per liter of bicarbonate ion, and about 75 to about 150 millimoles per liter of chloride ion, and is maintained at an osmolality within the range of from about 170 to about 460 and a pH in the range of from about 6 to about 8.5 by said gaseous blanket.

14. The method of claim 13 wherein said gaseous mixture is maintained at one atmosphere pressure and the partial pressure of said carbon dioxide therewithin is maintained in the range of from about 0.0007 to about 0.92 atmospheres.

15. A method of stabilizing the osmolality and pH of an aqueous therapeutic solution at desired levels, wherein said solution comprises about 75 to about 150 millimoles per liter of sodium cation, from about 5 to about 50 millimoles per liter of potassium cation, about 5 to about 50 millimoles per liter of bicarbonate ion and about 75 to about 150 millimoles per liter of chloride ion and has an osmolality in the range of from about 170 to about 460, and a pH in the range of from about 6 to about 8.5, said method comprising maintaining a blanket of gaseous mixture over said solution at a pressure of one atmosphere, said gaseous mixture comprising carbon dioxide and an inert gas, the carbon dioxide being preset in an amount sufficient to impart substantially equal pressure to the partial pressure of carbon dioxide from said solution due to equilibrium within said solution at a temperature in the range of from about 25° to about 50° C.

* * * * *